United States Patent [19]
Sugihara et al.

[11] Patent Number: 5,761,269
[45] Date of Patent: Jun. 2, 1998

[54] X-RAY COMPUTERIZED TOMOGRAPHY SYSTEM HAVING COOLING FEATURES

[75] Inventors: Naoki Sugihara; Hisashi Tachizaki; Tomiya Sasaki, all of Tochigi-ken; Yutaka Sata, Tokyo-to; Koichiro Kawano, Kanagawa-ken, all of Japan

[73] Assignee: Kabushiki Kaisha Toshiba, Kawasaki, Japan

[21] Appl. No.: 697,566

[22] Filed: Aug. 28, 1996

[30] Foreign Application Priority Data

Aug. 29, 1995 [JP] Japan ................... 7-220638
Apr. 17, 1996 [JP] Japan ................... 8-095603

[51] Int. Cl.$^6$ .................................................. A61B 6/03
[52] U.S. Cl. .................................. 378/199; 378/4; 378/200
[58] Field of Search .......................... 378/4, 15, 199, 378/200

[56] References Cited

U.S. PATENT DOCUMENTS 4,969,167  11/1990  Zupancic et al.
5,299,249   3/1994  Burke et al. .................... 378/15
5,610,968   3/1997  Deucher et al. ............... 378/200 X

FOREIGN PATENT DOCUMENTS 59-14604    1/1984  Japan.
07-313500  12/1995  Japan .......................... 378/199

*Primary Examiner*—David P. Porta
*Attorney, Agent, or Firm*—Oblon, Spivak, McClelland, Maier & Neustadt, P.C.

[57] ABSTRACT

An X-ray CT system includes a fixed frame portion and a rotating frame portion. Being provided with X-ray tubes, the rotating frame portion is arranged so as to rotate with respect to the fixed frame portion. Vane members for feeding air are secured on the rotating frame portion. In operation, with the rotation of the vane members together with the rotating frame portion, cool air is introduced into the rotating frame portion. Consequently, heated instruments, such as the X-ray tubes, in the rotating frame can be cooled down effectively.

8 Claims, 14 Drawing Sheets

FIG.7A  FIG.7B
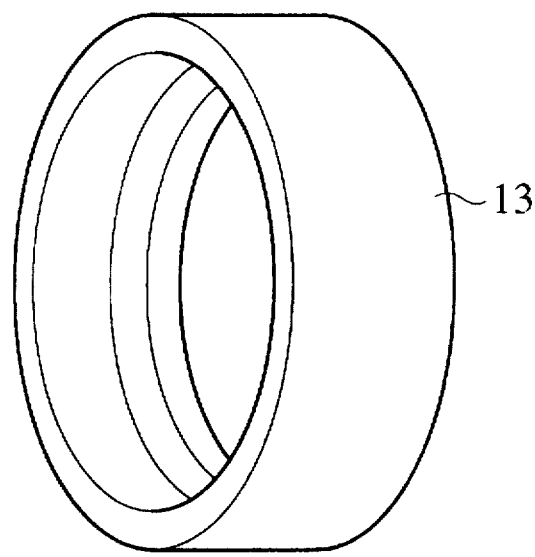
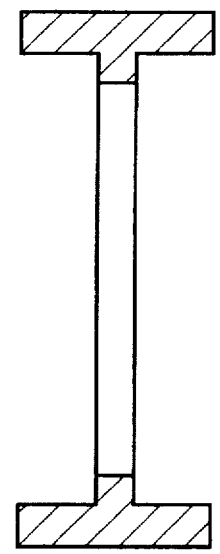
FIG.8
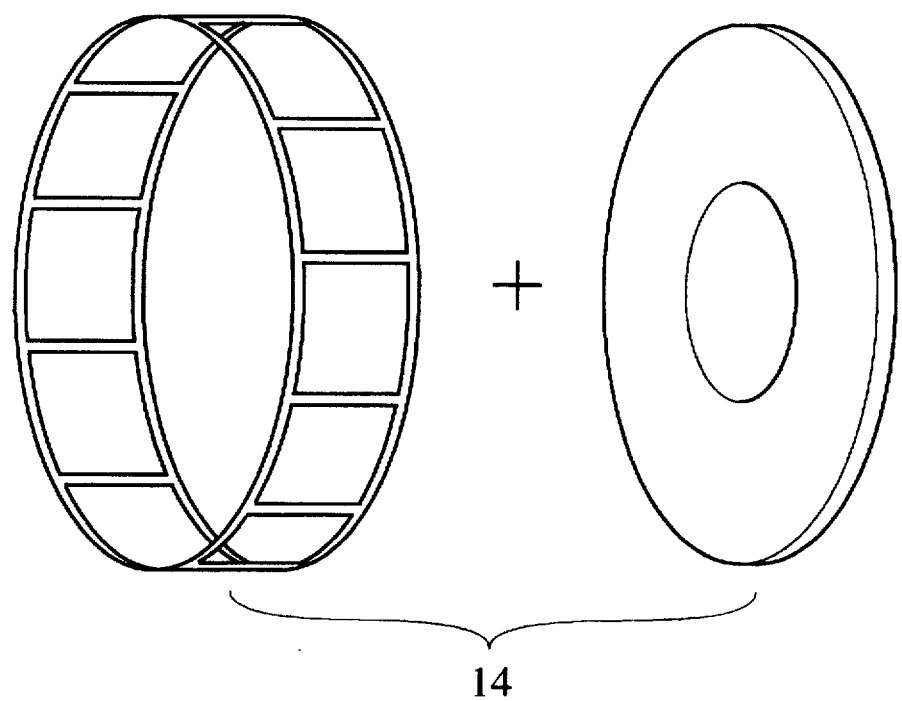

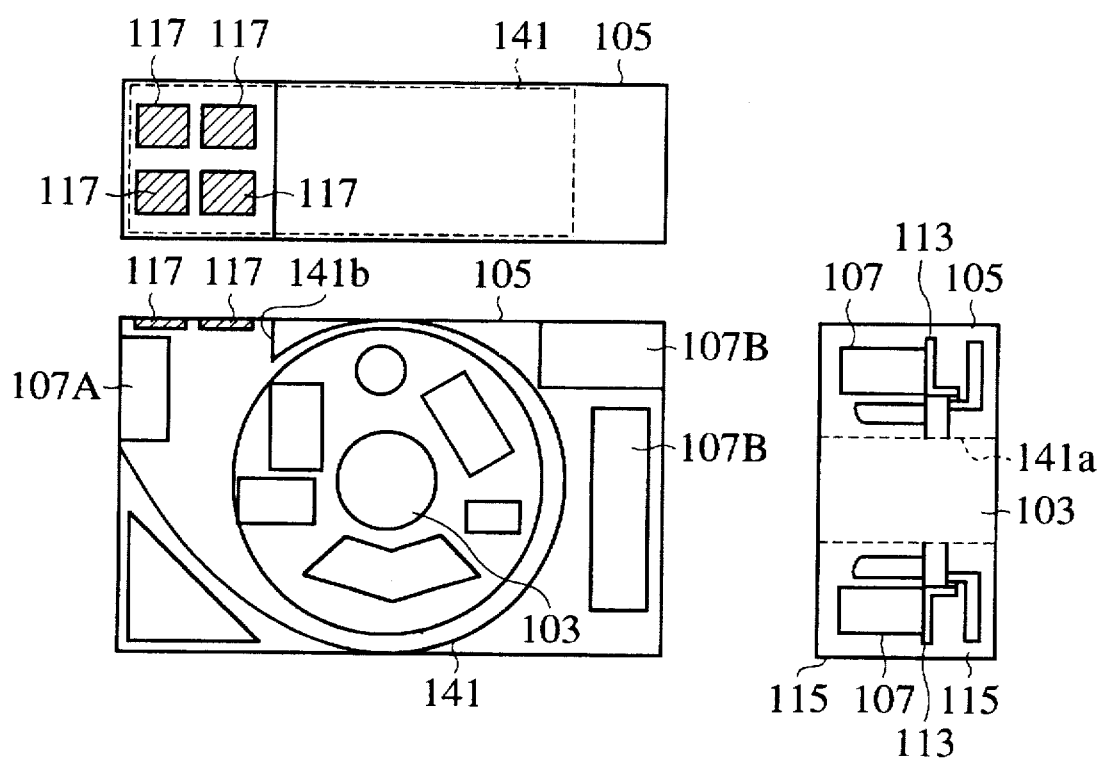

X-RAY COMPUTERIZED TOMOGRAPHY SYSTEM HAVING COOLING FEATURES

BACKGROUND OF THE INVENTION

1. Field of the Invention

The present invention relates to a CT (computerized tomography) system and, more particularly, to a CT system capable of effectively cooling the heat generated therein.

2. Description of the Related Art

In the prior art, the conventional X-ray CT system as a medical diagnostic system includes a frame which is so constructed that a patient examination region (i.e., radiographic port) used to pick up images of a subject is formed in the central portion. X-ray tubes, detectors, power sources, and signal processing parts are put in covers, i.e., box-like housing members' so as to put the radiographic port therebetween, so that part having the X-ray tubes, the detectors, the power sources, and the signal processing parts may be rotated around the subject. In order to prevent reduction in performance of the X-ray tubes, the detectors, etc. due to heat, cooling fans are provided in the cover or the frame.

A cooling method employed in the related art, is exemplified in the X-ray CT system set forth in Utility Model Application Publication (KOKAI) 59-14604, there has been proposed a method wherein suction ports are provided around a full periphery of a drum (radiographic port) in which a subject is to be inserted and then outside air is introduced into a cover by virtue of differential pressure generated by rotation of the rotating body (i.e., mounted parts serve as vanes of the centrifugal fan and air flows from the rotating body to the radial direction), and a method wherein ducts are provided so as to take in an outside air. In the X-ray CT system set forth in the U.S. Pat. No. 4,969,167, cooling ducts and nozzles are provided on an inner surface of a front cover and detectors are cooled in a concentrated manner by blowing air to detectors fixed around the examination area (fourth-generation X-ray CT system). Cooling air is supplied by fans, pumps, or other air supplying means.

More recent X-ray CT systems have been improved in performance and used in various applications by nature of the improvement in performance. An amount of generated heat is increased relative to other systems because of improvements in functionality and application and therefore it is insufficient for the above described cooling methods to cool the X-ray CT system. For instance, as shown in FIG. 1, in many conventional X-ray CT systems 201, parts 207 such as X-ray tubes, detectors and the like are provided on the rotating body 205, which has in a central portion a radiographic port 203 into which the subject is inserted, suction ports 209 in the side surface or the bottom, and cooling fans 211 on the side surface or the ceiling of the frame and the cover. Thus forced air cooling is effected by flowing air from the lower side to the upper side, as indicated by an arrow in FIG. 1. During operation of the X-ray CT systems, two airflows are generated, i.e., airflow caused by rotation of the rotating body 205 in the radial direction and airflow rotating in the frame in the same direction to the rotation. FIG. 2 is a graph illustrating the static pressure vs. flow rate of air characteristic generated by the rotational body in the rotational direction when the rotating body of a diameter of 1.5 (m) is rotated at a revolution speed of 60 (rpm), which is a model close to the condition of the frame of the usual X-ray CT system. As shown in FIG. 2, it can be understood that a large flow rate of air can be obtained if static pressure is low, while the flow rate of air is reduced if static pressure is high.

Cooling air is supplied from the lower area and side area of the frame 205 by the cooling fan and rotation of the rotating body 205. In this case, airflow of this cooling air collides with airflow caused in the rotational direction to generate stagnant areas A of air (it generates on the right side if the rotating body rotates in the clockwise direction), as shown in FIG. 1. Thus there is caused such a drawback that a cool air has a difficult time entering into the central portion of the rotating body 205, so that it becomes hard to exhaust heat generated in the central portion to outside of the X-ray CT system.

In the X-ray CT system set forth in the above described Utility Model Application Publication (KOKAI) 59-14604, since suction ports are provided around a full periphery of the radiographic port, it is probable that a contrast medium injected into the subject, or blood enter from the patient may enter the frame although the above drawback seems to be overcome. In addition, in the X-ray CT system set forth in the U.S. Pat. No. 4,969,167, only detectors could be cooled, but X-ray tubes which generate a large amount of heat could not be cooled. Especially, since X-ray tubes are rotated inside of the detector ring in the fourth-generation X-ray CT system, cooling air could not cool the X-ray tubes in compliance with the cooling method which is proposed herein.

SUMMARY OF THE INVENTION

The present invention has been made in light of the above problems, and it is an object of the present invention to provide an X-ray CT system capable of efficiently maintaining an inside of a frame to within a predetermined temperature range under increased heat conditions associated with improved functionality and application of the X-ray CT system and other various working conditions.

In order to achieve the above object, and according to an aspect of the present invention, there is provided an X-ray CT system having:

a frame fixing portion;

a frame rotating portion arranged rotatably to the frame fixing portion; and means for feeding an air by rotating vane members secured to the frame rotating portion together with the frame rotating portion.

In this structure, cooling by means of suitable air circulation can be achieved at low noise, and no ceiling fan is required.

The above X-ray CT system may further includes:

means for controlling flow rate of air fed by the feeding means in accordance with rotational speed of the frame rotating portion. Thereby, suitable flow rate control can be implemented.

According to another aspect of the present invention, there is provided an X-ray CT system having:

a rotating body arranged to be rotated around a subject with the subject as a center, and having a plurality of X-ray tubes arranged around a through hole in which the subject is to be inserted; and a frame for housing the rotating body therein, and having a radiographic port which is arranged in compliance with the though hole to pick up images of the subject;

wherein suction ports are arranged in the radiographic port so as to introduce an air into the frame.

Thereby, an inside of the frame can be maintained in a predetermined temperature range with good efficiency under increased heating amount condition because of improved function and application of the X-ray CT system and other various working conditions.

According to still another aspect of the present invention, there is provided an X-ray CT system comprising:

a rotating body arranged to be rotated around a subject with the subject as a center, and having a plurality of X-ray tubes arranged around a through hole in which the subject is to be inserted; and a frame for housing the rotating body therein, and having a radiographic port which is arranged in compliance with the though hole to pick up images of said subject;

wherein at least part of the radiographic port is formed as a double wall structure in which suction ports for the radiographic port are provided to introduce an air into the frame.

In the X-ray CT system of the preferred embodiment, at least part of an upper half of said radiographic port is formed as a double wall structure, and suction ports for the radiographic port are provided in the double wall structure so as to introduce the air into the frame.

Thereby, an inside of the frame can be effectively maintained in a predetermined temperature range under increased heat conditions owing to improved functionality and application of the X-ray CT system and other various working conditions.

According to yet still another aspect of the present invention, there is provided an X-ray CT system having:

a rotating body arranged to be rotated around a subject with the subject as a center, and having a plurality of X-ray tubes arranged around a through hole in which the subject is to be inserted; and a frame for housing the rotating body therein, and having a radiographic port which is arranged in compliance with the though hole to pick up images of the subject;

wherein guide plates are arranged in the frame to guide airflow.

In this X-ray CT system of the preferred embodiment, the guide plates to guide airflow are provided in the frame. Thereby, an inside of the frame can be effectively maintained in a predetermined temperature range under increased heat conditions owing to improved functionality and application of the X-ray CT system and other various working conditions.

According to further aspect of the present invention, there is provided an X-ray CT system having:

a rotating body arranged to be rotated around a subject with the subject as a center, and having a plurality of X-ray tubes arranged around a through hole in which the subject is to be inserted;

a frame for housing the rotating body therein, and having a radiographic port which is arranged in compliance with the though hole to pick up images of the subject; and a casing arranged in the frame to cover the rotating body, the casing having suction ports arranged on the radiographic port side so as to introduce air and delivery ports arranged toward the rotation direction of the rotating body to discharge the air;

wherein holes are arranged in said radiographic port to coincide with the suction ports and holes are arranged in the frame so as to coincide with the delivery ports.

BRIEF DESCRIPTION OF THE DRAWINGS

FIG. 7A is a perspective view showing a third modification of the cylindrical supporting member according to the first embodiment of the present invention;

FIG. 7B is a sectional view showing the third modification in FIG. 7A;

FIG. 8 is a perspective view showing a fourth modification of the cylindrical supporting member according to the first embodiment of the present invention;

FIG. 21A is a front view showing in section an X-ray CT system according to a fifth embodiment of the present invention;

FIG. 21B is a plan view showing the X-ray CT system in FIG. 21A; and

FIG. 21C is a side view showing in section the X-ray CT system in FIG. 21A.

DETAILED DESCRIPTION OF THE PREFERRED EMBODIMENTS

There will be explained preferred embodiments of the present invention with reference to accompanying drawings hereinafter.

Figure 3:
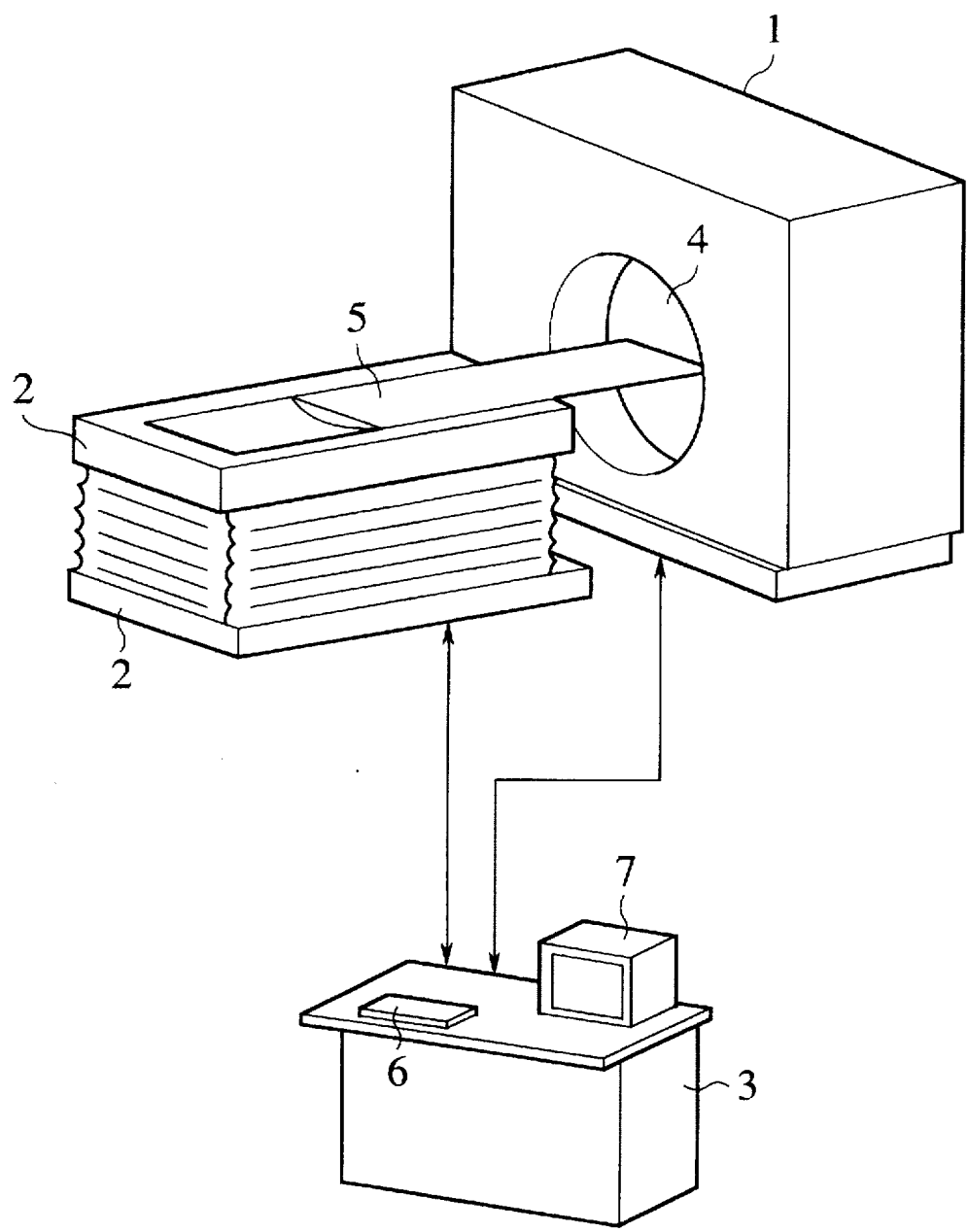
FIG. 3 is a perspective view showing an appearance of an X-ray CT system according to a first embodiment of the present invention.

Explanation will first be made of a first embodiment of the present invention hereinbelow. FIG. 3 is a perspective view showing an appearance of an X-ray CT system according to the first embodiment of the present invention. The X-ray CT system of the first embodiment is composed of a frame 1, a bed 2, and a console 3. An opening portion 4 in which a subject is to be inserted is formed in the center of the frame 1. The bed 2 is arranged in front of the frame 1. The bed 2 is so formed that its height can be adjusted by a motor. A top plate 5 on which the subject is loaded is provided on the bed. The top plate 5 can slide across the fixed frame 1 by means of a motor. A keyboard 6 (including a mouse) and a CRT monitor 7 are placed on the console 3. A controlling portion which is connected to both the frame 1 and the bed 2 to control their operations is housed in the console 3.

The frame 1 consists of a frame fixing portion and a frame rotating portion. The frame rotating portion is supported rotatably to the frame fixing portion. To the frame rotating portion are provided the above various units ($20_0$ to $20_4$), i.e., X-ray tubes for irradiating sectorial X-ray beams to the subject loaded on the top plate 5, a plurality of detector arrays arranged in a circular arc with a focus of the X-ray tubes as a center to detect the X-ray passed through the subject on a multi-channel basis, and the like.

Figure 4A:
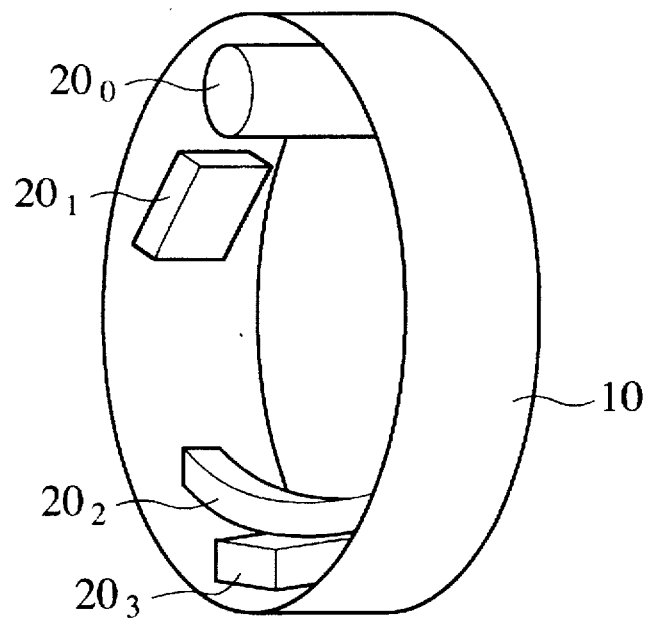
FIG. 4A is a perspective view showing a structure of a cylindrical supporting member for a frame rotating portion of the X-ray CT system according to the first embodiment of the present invention.
Figure 4B:
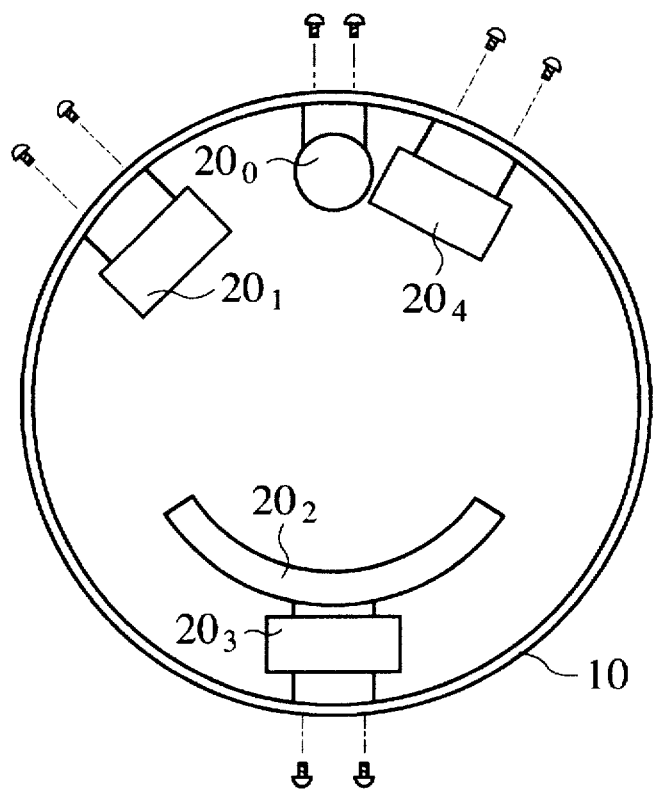
FIG. 4B is a side view showing the structure of the cylindrical supporting member in FIG. 4A.

In more detail, in the first embodiment, as shown in FIG. 4A, the frame rotating portion has a cylindrical supporting member 10, and respective units ($20_0$ to $20_4$) are attached to the inner wall of the supporting member 10. As shown in FIG. 4B, each unit 20 is screwed in the radial direction. Each unit 20 is electrically connected to the frame fixing portion unit 20 via a slip ring. On the frame fixing portion are provided devices for supplying electric cower, control signals, etc. to respective units 20 fixed to the frame rotating portion via the slip ring.

With the above structure, even when the frame rotating portion rotates at high speed to thus exert a vast centrifugal force on respective units, respective units 20 can be fixed to the supporting member 10 with a strong fixing force. Accordingly, the frame rotating portion is enabled to rotate in the frame fixing portion at higher speed, which may contribute to shortened of scan time (for example, scan time within one second).

Figure 5:
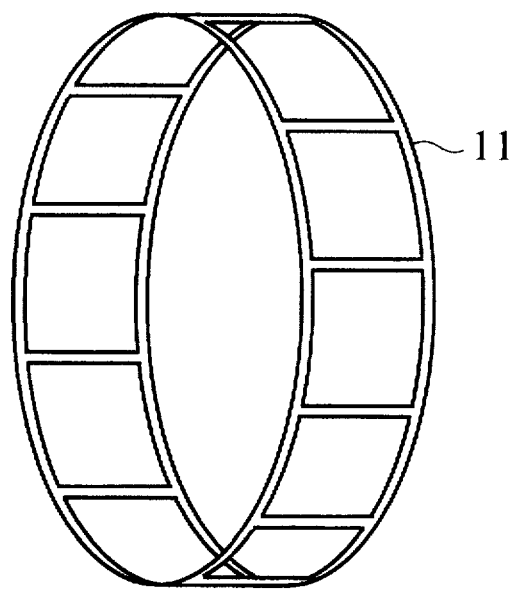
FIG. 5 is a perspective view showing a first modification of the cylindrical supporting member according to the first embodiment of the present invention.
Figure 6A:
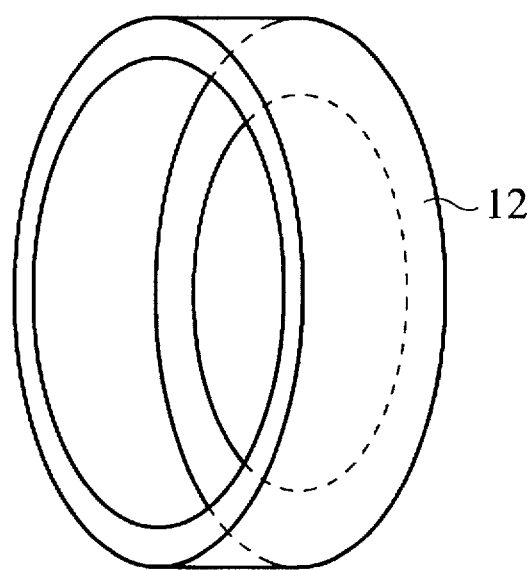
FIG. 6A is a perspective view showing a second modification of the cylindrical supporting member according to the first embodiment of the present invention.
Figure 6B:
FIG. 6B is a sectional view showing the second modification in FIG. 6A.

As another structure of the cylindrical supporting member 10 on an inner wall of which the units are attached, there may be considered a frame-like supporting member 11 formed by combining pipe-like members as shown in FIG. 5, a cylindrical supporting member 12 with a bottom as shown in FIGS. 6A and 6B, a supporting member 13 as shown in FIGS. 7A and 7B, or a supporting member 14 as shown in FIG. 8.

Figure 9A:
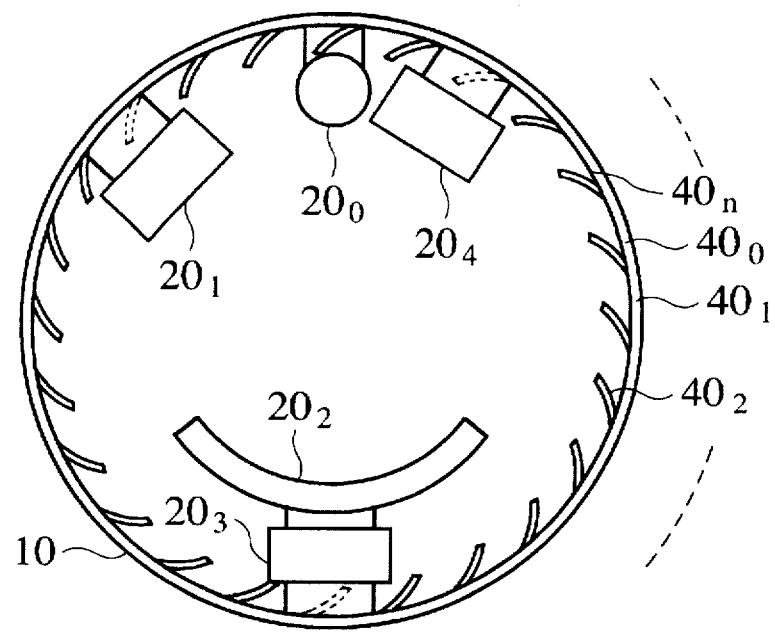
FIG. 9A is a side view showing a structure for attaching vane members to the cylindrical supporting member according to the first embodiment of the present invention.
Figure 9B:
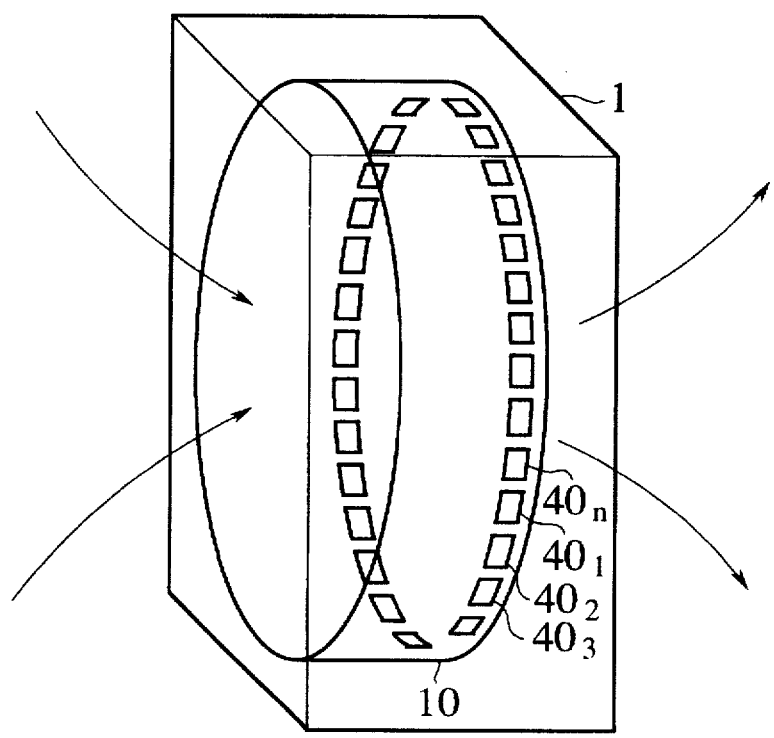
FIG. 9B is a perspective view showing the structure in FIG. 9A.
Figure 10B:
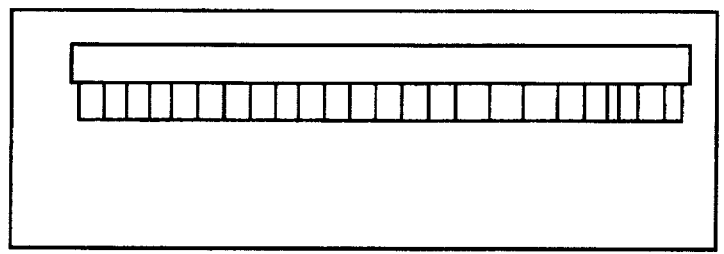
FIG. 10B is a side view showing the structure in FIG. 10A.
Figure 10A:
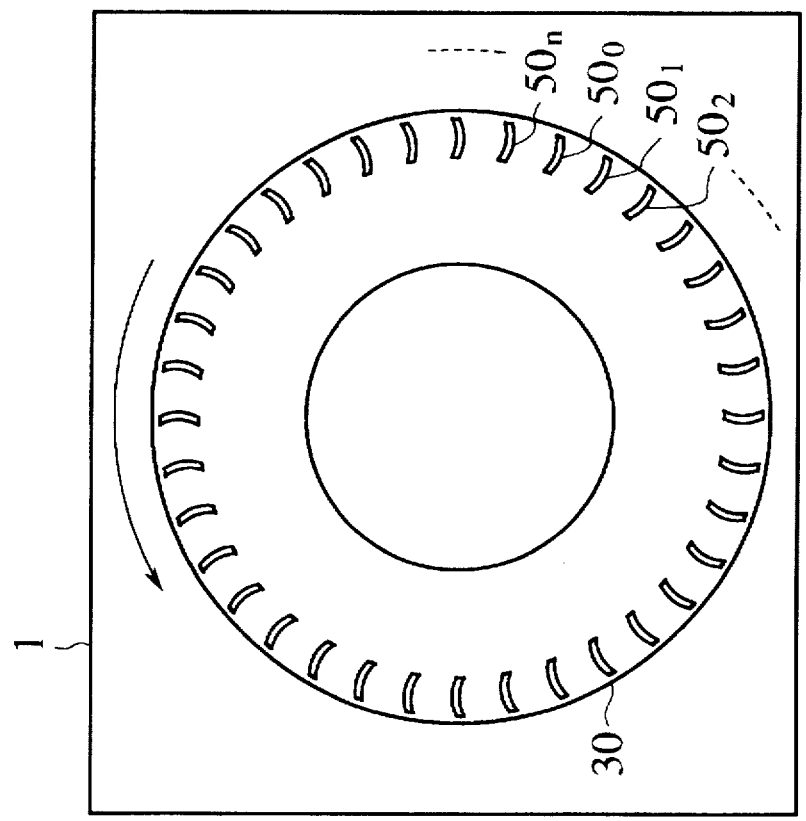
FIG. 10A is a front view showing a structure for attaching vane members to a disk-type supporting member according to the first embodiment of the present invention.

In the meanwhile, if the above structure in which respective units are fixed to the cylindrical supporting member is employed, the inside of the frame is filled with heat generated when the X-ray CT system according to the first embodiment operates to drive respective units. As a result, the inside of the frame cannot be cooled down by the conventional ceiling fan which is provided with the frame fixing portion. Therefore, in the first embodiment, as shown in FIGS. 9A and 9B, a plurality of vane members $40_0$, $40_1$, ...., $40_n$ are provided on an inner surface of the cylindrical supporting member 10. Thus by rotating these vane members 40 together with the frame rotating portion to blow an air, heat is then radiated from the inside of the cylindrical supporting member. For this reason, heat can be removed from the inside of the frame without the ceiling fan, so that the noises caused by the ceiling fan can be eliminated. In the event that the supporting member to which the units are attached is formed as a disk-like supporting member 30 in place of cylindrical supporting member 10, vane members $50_0$, $50_1$,.... $50_n$ can be arranged on the disk-like supporting member 30, as shown in FIGS. 10A and 10B, to blow an air. Thus this enables the inside of the frame to be cooled without the ceiling fan.

Figure 11:
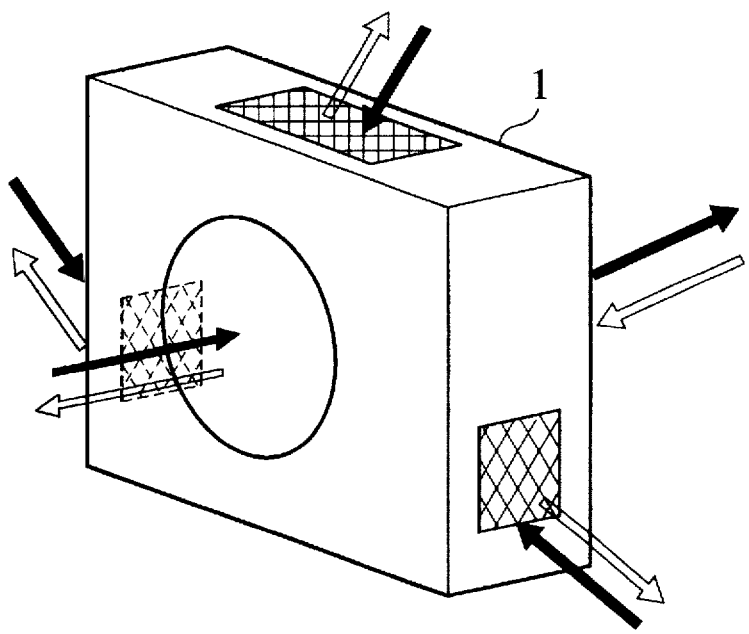
FIG. 11 is a perspective view illustrating the directions of airflow in the first embodiment of the present invention.
Figure 12:
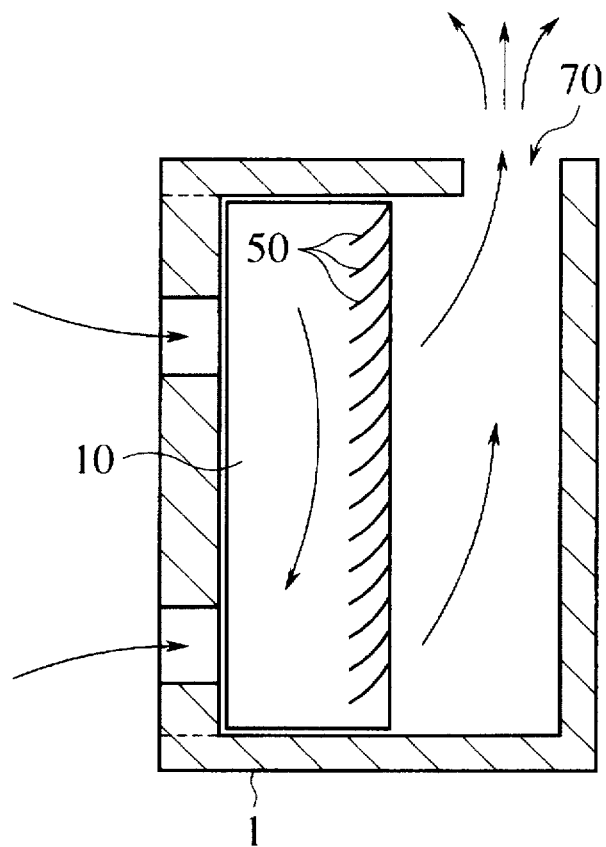
FIG. 12 is a sectional view showing a structure to suck in air from outside and exhaust the air in the first embodiment of the present invention.

The direction blown air may be determined arbitrary in accordance with the direction of vane members and rotational direction of the frame rotating portion. For instance, as shown in FIG. 11, such direction may be selected in the direction indicated by white arrows or black arrows. As for suction (or exhaustion) of the air, as shown in FIG. 12, the air may be sucked (or delivered) from (or to) the desired direction by providing a duct 70, for example.

Figure 13:
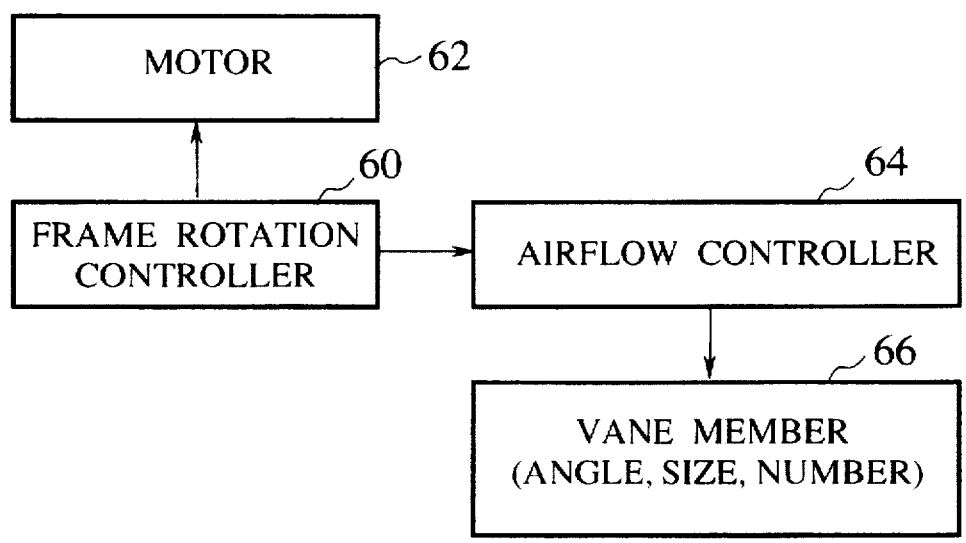
FIG. 13 is a block diagram illustrating an example to control an amount of airflow in compliance with rotational speed of the frame rotating portion according to the first embodiment of the present invention.

As for an amount of airflow, it may be controlled in response to rotational speed of the frame rotating portion. FIG. 13 is a block diagram showing an example to control an amount of airflow in compliance with rotational speed of the frame rotating portion. Rotational speed of motor 62 for rotating the frame rotating portion is controlled by a frame rotation controlling portion 60. At this time, information of the rotational speed is sent to an airflow controller 64. The airflow controller 64 may control vane members 66 which are so formed that angle, size and number thereof can be controlled. With the above construction, airflow control may be effected more suitably.

More particularly, the angle may be controlled by rotating the vane members 66, the size may be controlled by changing a flap projection amount of the vane members 66, and the number of the vane members 66 may be controlled by folding the desired number of the vane members 66. By carrying out control of flow rate in this manner, noise can be suppressed quietly and over cooling of temperature-controlled parts can be prevented. For instance, since the detector unit is heated at a predetermined temperature to obtain its optimal sensitivity, over cooling of the detector unit should be prevented.

Figure 14:
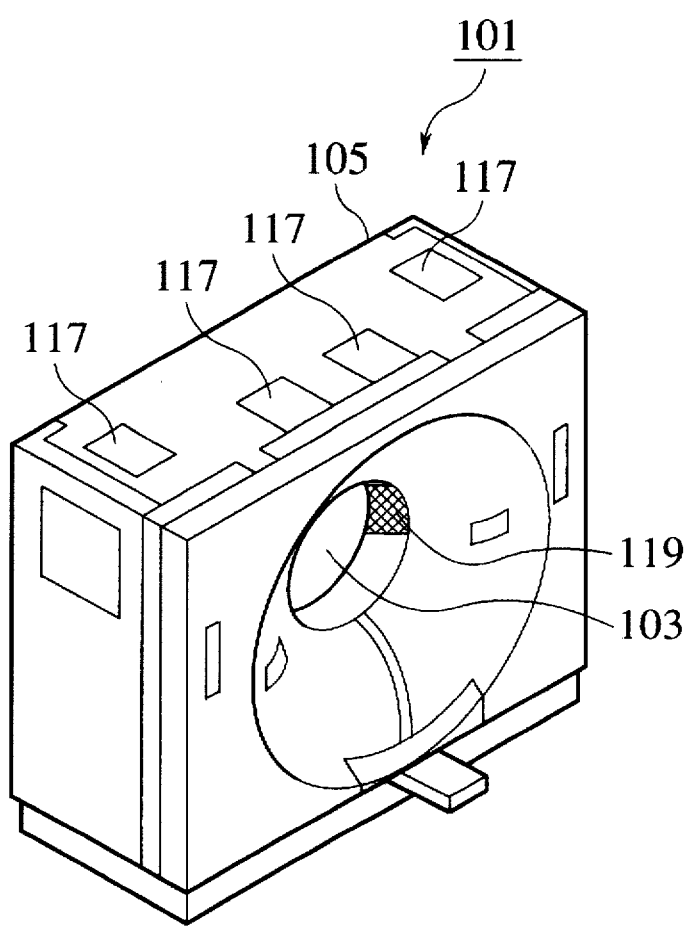
FIG. 14 is a perspective view showing an X-ray CT system according to a second embodiment of the present invention.
Figure 15:
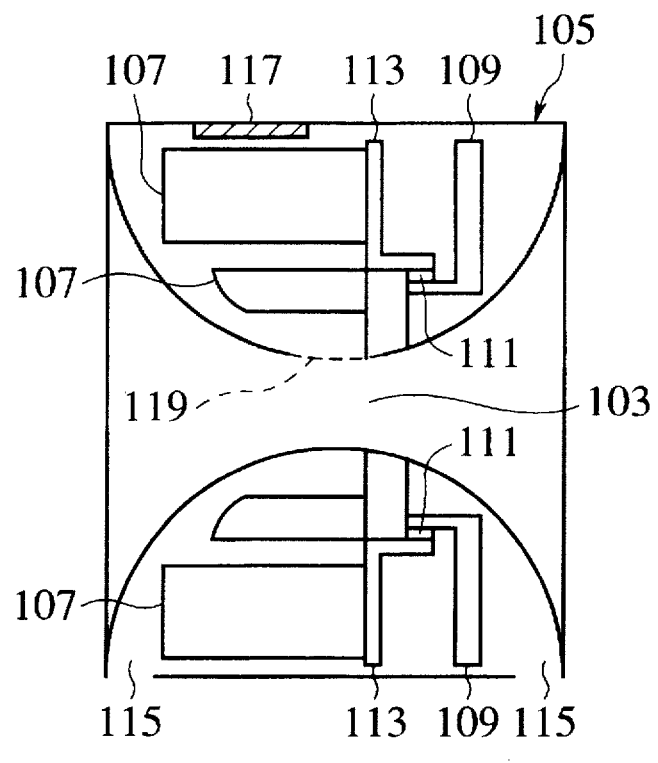
FIG. 15 is a sectional view showing the X-ray CT system according to the second embodiment of the present invention.

Explanation will next be made of a second embodiment of the present invention hereinbelow. FIG. 14 is a perspective view showing an X-ray CT system according to the second embodiment of the present invention. FIG. 15 is a sectional view showing the X-ray CT system in FIG. 14.

As shown in FIG. 14, a frame of an X-ray CT system 101 is so constructed that a radiographic port 103 used to pick up images of a subject is formed in the central portion, parts 107 such as X-ray tubes, detectors, power sources, and signal processing means are put in a frame 105, i.e., box-like housing members so as to put the radiographic port 103 therebetween. In the X-ray CT system 101, as shown in FIG. 15, part of the parts 107 such as the X-ray tubes, the detectors, the power sources, and the signal processing parts are secured to a rotating body 113 which is attached rotatably to a base 109 fixed to the frame 105 via a bearing 111, so that they are rotated around the subject. FIG. 15 shows a sectional shape in the direction perpendicular to opening surface of the radiographic port 103.

Figure 16:
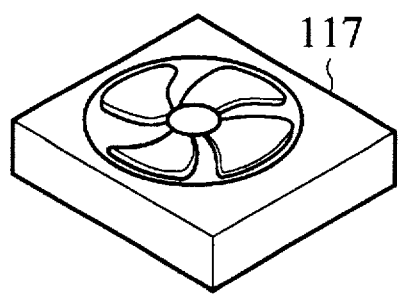
FIG. 16 is a perspective view showing a cooling fan used in the second embodiment of the present invention.

Since the X-ray tubes, the power sources, control substrates, etc. in the parts 107 of the X-ray CT system 101 generate heat. reduction in performance of the parts 107 such as the X-ray tubes, the detectors, etc. due to heat would occur unless such heat is radiated (cooled). Therefore, in order to prevent such reduction in performance of the parts 107, suction ports 115 are provided in the lower portion of the frame 105 to introduce an outside air while cooling fans shown in FIG. 16 are provided in the upper portion of the frame 105. Plural cooling fans 117 are provided, and flow rate of the air can be adjusted if the number of the cooling fans 117 is varied.

Particularly, in the second embodiment, the suction ports 119 for the radiographic port may be provided in the upper half (in the range between nine o'clock to three) of the central portion of the radiographic port 103. For safety's sake, a mesh-like protection cover or a porous protection cover with an open area ratio of more than 50% should be provided on the suction ports 119 for the radiographic port. In the second embodiment, the suction ports 119 for the radiographic port may be provided in the upper half (in the range between nine o'clock to three) of the central portion of the radiographic port 103, but they are not limited to this example. If they are provided in the upper half portion of the radiographic port 103, they may be provided in not only the central portion but also peripheral portion, for example, and in addition they may be provided in the range between ten o'clock to two. Although the open area ratio of the suction ports 119 for the radiographic port is set to more than 50%, it is not limited to this value. In order to introduce an outside air, the open area ratio of more than 20% is required at the lowest.

If flow of heat and air in the X-ray CT system 101 is watched in an examination waiting state (when no X-ray is irradiated), a cool outside air is introduced by the cooling fans 117 from the suction port 115 and the suction ports 119 for the radiographic port into the X-ray CT system 101 to absorb heat generated by the parts 107. Then, warmed air is discharged by the cooling fan 117 out of the X-ray CT system 101.

In an examination state (when X-rays are irradiated) airflow is caused in the radial direction upon rotating the rotating body 113. However, since the cool air introduced from the suction port 115 provided in the lower portion collides with airflow caused by rotation of the rotating body 113 (such collision occurs on the right side in the case of clockwise rotation) to prevent the cool air from entering into the central portion of the rotating body 113, cool air has a difficult time entering the central portion of the rotating body 113. Therefore, heat generated by the parts 107 in the central portion cannot be exhausted from the X-ray CT system 101.

However, in the second embodiment, because the suction ports 119 for the radiographic port is provided in the radiographic port 103, heat generated by the parts 107 in an inside portion of the rotating body 113 can be effectively cooled down by airflow generated by the cooling fan 117 and a rotating force of the rotating body 113 in the radial direction.

In the second embodiment, since the suction ports 119 for the radiographic port is provided in the upper half of the radiographic port 103, contrast medium which is injected into the subject in some cases at the time of examination, blood, etc. never enters into the frame 105. As a result, the X-ray CT system 101 can operate safely at that time. In addition, the number of the cooling fans (not shown) provided in the parts 107 such as X-ray tubes, detectors, power sources, and signal processing means secured to the rotating body 113 can be reduced, and the number of cooling fans 117 provided in the upper portion of the X-ray CT system 101 can be reduced.

Like the above, in the second embodiment, since the suction ports 119 for the radiographic port is provided in the upper half of the radiographic port 103, an inside of the frame 105 can be efficiently kept in a predetermined temperature range under increased heat conditions because of improved function and application of the X-ray CT system and other various working conditions.

Explanation will then be made of a third embodiment of the present invention hereinbelow.

Figure 17:
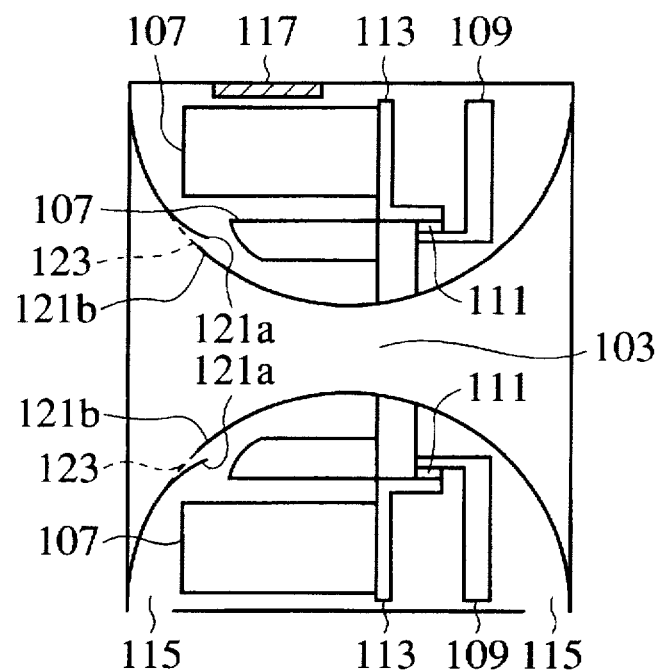
FIG. 17 is a sectional view showing an X-ray CT system according to a third embodiment of the present invention.

FIG. 17 is a sectional view showing an X-ray CT system according to the third embodiment of the present invention. In the third embodiment, instead of the suction ports 119 for the radiographic port in the second embodiment shown in FIGS. 14 and 15, as shown in FIG. 17, at least part of the radiographic port 103 is formed as a double wall structure, and the suction ports 123 for the radiographic port are provided in this double wall structure. Since remaining structures of the third embodiment are identical to the X-ray CT system 101 of the second embodiment shown in FIGS. 14 and 15, their detailed explanation are omitted by using like labels.

As shown in FIG. 17, the double wall structure of the radiographic port 103 is so formed that an inner wall 121a is formed in the lower portion of the radiographic port 103 by bending part of the wall of the radiographic port 103 upwardly and inwardly and then an outer wall 121b is formed in the radiographic port 103 downwardly so as to overlap (but not contact to) part of the inwardly bent portion of the inner wall 121a. In this event, an area formed between the front end portion of the outer walls 121b and the base of the inner wall 121a may serve as the suction ports 123 for the radiographic port. Like the suction ports 119 for the radiographic port, the protection cover is also provided on the suction port 123 for the radiographic port. In the same manner, the suction port 123 for the radiographic port is formed in the upper portion of the radiographic port 103.

Although the suction ports 123 for the radiographic port are formed in both the lower and upper portions of the radiographic port 103, the suction ports 123 are not to the above. The suction port 123 may be formed in at least the upper portion and the lower portion of the radiographic port 103.

At this time, since the suction port 123 for the radiographic port formed in the lower portion of the radiographic port 103 is directed downwardly in the inside of the frame, contrast medium by no means enters the frame 105 even if contrast medium is spilt on the radiographic port 103.

In this fashion, in the third embodiment, since at least part of the radiographic port 103 is formed as a double wall structure and the suction ports 123 for the radiographic port are provided in this double wall structure, an inside of the frame 105 can be efficiently maintained in a predetermined temperature range with good efficiency under increased heat conditions because of improved function and application of the X-ray CT system and other various working conditions.

Figure 18:
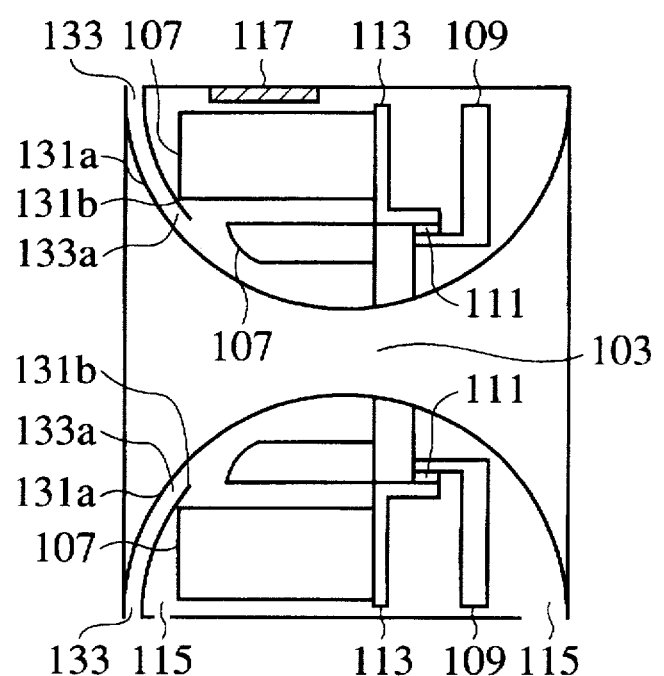
FIG. 18 is a sectional view showing a double wall structure of a radiographic port in the third embodiment of the present invention.

In the third embodiment, although, to form the double wall structure of the radiographic port 103, the inner wall 121a is formed in the lower portion of the radiographic port 103 by bending part of the wall of the radiographic port 103 upwardly and inwardly and then the outer wall 121b is formed in the radiographic port 103 downwardly so as to overlap part of the inwardly bent portion of the inner wall 121a, the present invention is not restricted to such structure. For purposes of example, part or all of the radiographic ports 103 may be formed as the double wall structure consisting of the outer wall 131a and the inner wall 131b, then the suction ports 123 for the radiographic port may be provided in at least one of the upper portion and the lower portion of the radiographic port 103, and then an air exhausting port 133a may be formed in the rotating body 113. In FIG. 18, a case is shown wherein part of the radiographic port 103 is formed as the double wall structure.

Explanation will then be made of a fourth embodiment of the present invention hereinbelow.

Figure 19:
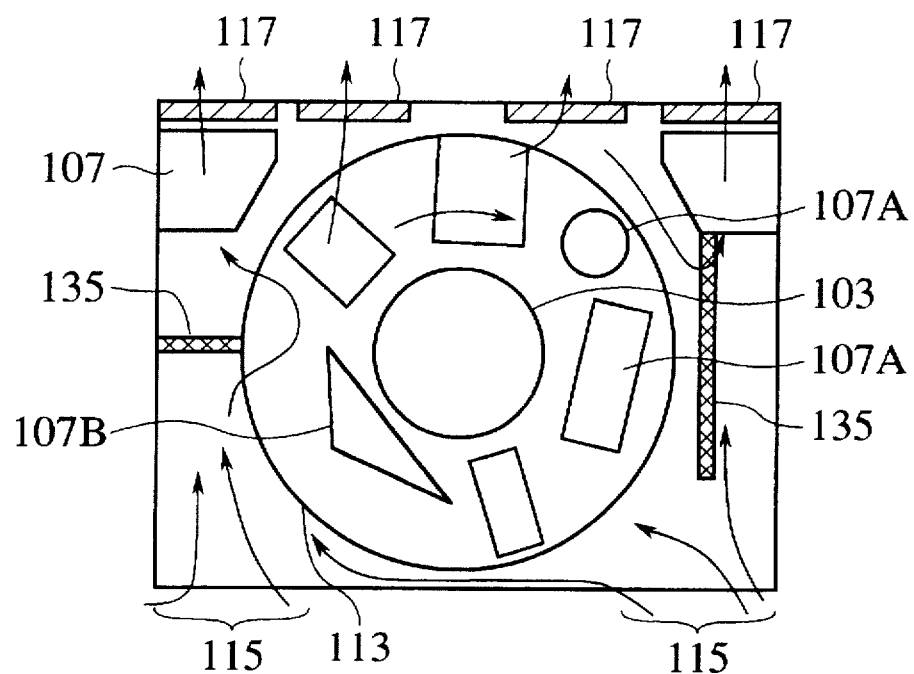
FIG. 19 is a sectional view showing an X-ray CT system being equipped with guide plates according to a fourth embodiment of the present invention.

FIG. 19 is a sectional view showing an X-ray CT system being equipped with guide plates according to the fourth embodiment of the present invention. FIG. 19 is a front view showing in section the X-ray CT system in a state where a front cover of the frame is removed. In FIG. 19, like references in FIGS. 14 and 15 identify like parts in FIGS. 14 and 15 and thus their detailed explanations are omitted.

Since heat generating parts 107A such as X-ray tubes, power sources, control substrates, etc. and non-heat generating parts 107B such as detectors are provided separately in the frame 105 of the X-ray CT system 101, performance of the parts 107 is lowered unless the heat generating parts 107A are cooled. Cooling air is supplied from the lower area and side area of the frame 105 by the cooling fan 117 and rotation of the rotating body 113. At this time, airflow of this cooling air collides with airflow caused in the rotational direction so as to generate stagnant areas of air (on the right side if the rotating body rotates in the clockwise direction). Thus, cool air has a difficult time entering into the central portion of the rotating body 113. As a result, it becomes difficult to exhaust heat generated by the heat generating parts 107A such as X-ray tubes, power sources, control substrates, etc. to outside of the X-ray CT system 101. In the fourth embodiment, by providing guide plates 135 for guiding airflow in the frame 105, airflow if forcibly guided to flow into the rotating body 113 side and to eliminate the stagnant areas of air.

The guide plates 135 are placed between an inside surface of the frame 105 and the rotating body 113 in the wide space without the parts 107 in the frame 105. In the example in FIG. 19, the guide plates 135 are placed between a left side surface of the frame 105 and the rotating body 113.

The stagnant areas of air is generated on the right side of the frame 105 if the rotating body 113 is rotated clockwise. Hence, by providing the guide plates 135 in parallel to the side surface of the frame 105 on the rotating body 113 side in the right side of the frame 105 and also providing the cooling fans 117 on the top plate between the guide plates 135 and the right side surface of the frame 105, the air existing between the guide plates 135 and the right side surface of the frame 105 can be discharged by the cooling fans 117 out of the frame 105.

The guide plates 135 are desired to be provided throughout the front surface to the rear surface of the frame 105. But the guide plates 135 are not limited to the above if airflow is disturbed because of alignment of the parts 107 or if the guide plates 135 cannot be provided throughout the front surface to the rear surface of the frame 105 because of alignment of the parts 107.

Figure 1:
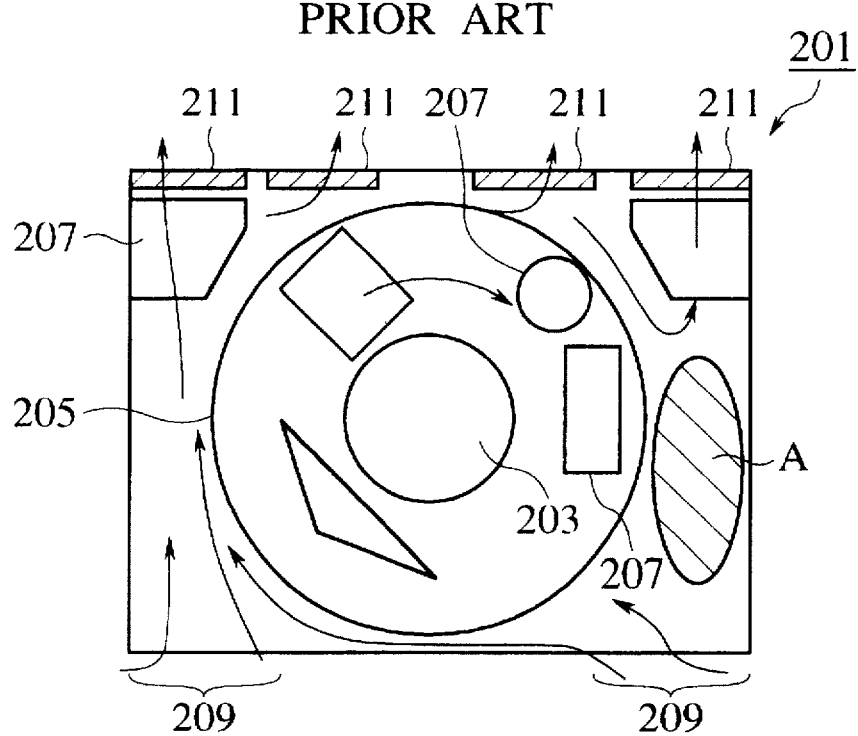
FIG. 1 is a schematic view showing a structure of a frame of a conventional X-ray CT system.
Figure 2:
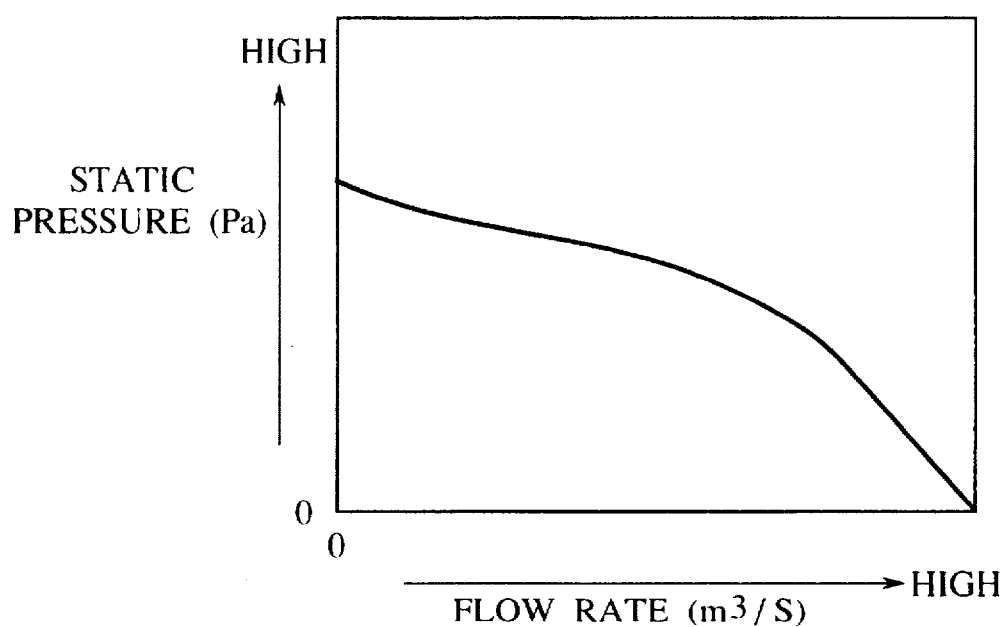
FIG. 2 is a graph illustrating the static pressure-flow rate of air characteristic of rotating body.

Airflow has already been illustrated in FIG. 1 when the frame is not equipped with the guide plates 135. Because parts 207 such as X-ray tubes, high voltage generating devices, signal processing means, etc. secured to the rotating body 205 may serve as vanes of the centrifugal fan, air in the frame is caused to flow in the radial direction. However, since the cooling air is introduced from the lower portion and the side surface of the frame, the airflow of the cooling air collides with the airflow generated by rotation of the rotating body to generate a stagnant area A and thus smooth airflow of the cooling air is achieved in the frame.

In this fourth embodiment, by providing the guide plates 135, the conventional stagnant area can be eliminated and also the cooling air is caused to flow into the central area of the rotating body 113, as indicated by arrows in FIG. 19. Therefore, heat generated in the central area of the rotating body 113 and the rotating mechanism can be discharged outside of the rotating body 113 and further outside of the frame 105. Consequently, an inside of the frame 105 can be maintained within a predetermined temperature range.

In this manner, in the fourth embodiment, since the guide plates 135 are provided to guide the airflow in the frame 105, an inside of the frame 105 can be maintained in a predetermined temperature range with good efficiency under increased heating amount condition because of improved function and application of the X-ray CT system and other various working conditions.

Figure 20:
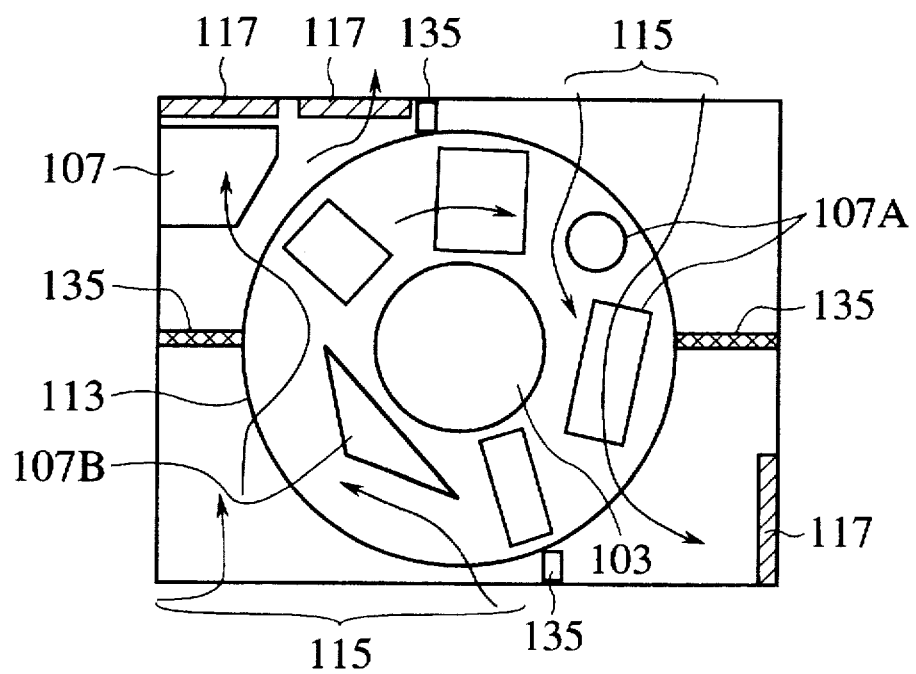
FIG. 20 is a sectional view showing a modification of the X-ray CT system being equipped with another guide plates according to the fourth embodiment of the present invention.

Alignment of the guide plates 135 is not limited to that in FIG. 19. In other words, for example, as shown in FIG. 20, the guide plates 135 may be arranged respectively between the left side surface of the frame 105 and the rotating body 113, between the right side surface of the frame 105 and the rotating body 113, between the upper surface of the frame 105 and the rotating body 113, and the lower surface of the frame 105 and the rotating body 113. FIG. 20 is a front view showing in section the X-ray CT system in a state where a front cover of the frame 105 is removed. In FIG. 20, like references in FIGS. 14 and 15 refer to like parts in FIGS. 14 and 15 and therefore their detailed explanations are omitted.

In this case, in order to eliminate stagnant area of the air, airflow is generated from upper right portion to the lower right side surface by providing the cooling fans 117 on the lower portion of the right side surface of the frame 105.

In this event, because of the guide plates 135, the conventional stagnant area can be eliminated and also the cooling air is caused to flow into the central area of the rotating body 113, as indicated by arrows in FIG. 20. Hence, heat generated in the central area of the rotating body 113 and the rotating mechanism can be discharged outside of the rotating body 113 and further outside of the frame 105. For this reason, an inside of the frame 105 can be maintained within a predetermined temperature range.

Explanation will now be made of a fifth embodiment of the present invention hereinbelow. FIG. 21A is a front view showing an X-ray CT system in a state where a front cover of the frame 105 is removed. FIG. 21B is a plan view showing the X-ray CT system in FIG. 21A. FIG. 21C is a side view showing in section the X-ray CT system in FIG. 21A (i.e., a sectional view when viewed from the direction perpendicular to the opening surface of the radiographic port 103). In FIGS. 21A to 21C, like references in FIGS. 14 and 15 designate like parts in FIGS. 14 and 15 and thus their detailed explanations are omitted.

In the fifth embodiment, a casing 141 is arranged in the frame 105 to cover the rotating body 113. The casing 141 has suction ports 141a arranged on the radiographic port 103 side and delivery ports 141b arranged in coincidence with the rotation direction of the rotating body 113 (in this embodiment, delivery ports 141b are provided on the upper left portion of the frame 105 since clockwise rotation is adopted). Thus airflow caused by the rotation of the rotating body 113 in the radial direction can be discharged smoothly out of the frame 105. In the casing 141, a through hole is formed in the central portion of the frame 105 to correspond to the radiographic port 103, the suction ports 141a are arranged on the radiographic port 103 side, and the delivery ports 141b are arranged in the upper left portion of the frame 105. The casing 141 covers the rotating body 113 and the entire parts 107 arranged on the rotating body 113 to wrap them from the upper left side (from the upper right side if the rotating body 113 rotates counterclockwise). (Ideally speaking, a profile of the casing 141 is formed as a logarithmic spiral curve).

The through hole is formed in the radiographic port 103 to coincide with the suction ports 141a whereas the through hole and the cooling fans 117 are formed in the frame 105 to coincide with the delivery ports 141b.

In the case of the fifth embodiment, since the rotating body 113 itself serves as the centrifugal fan because of the casing 141, airflow caused by rotation of the rotating body 113 in the radial direction can be discharged smoothly along the casing 141 to outside of the rotating body 113 and further outside of the frame 105.

In the area of the frame 105 except for the rotating body 113, heat generating parts 107A and non-heat generating parts 107B are arranged. Therefore, as shown in FIG. 21A, it is preferable that the heat generating parts 107A should be arranged in the casing 141 (near the delivery ports 141b if desired) and non-heat generating parts 107B should be arranged outside of the casing 141. Thereby, the heat generating parts 107A can be cooled effectively by virtue of the airflow caused by rotation of the rotating body 113 in the radial direction.

As stated above, in the fifth embodiment, since a casing 141 which covers the rotating body 113 and has suction ports 141a arranged on the radiographic port 103 side and delivery ports 141b arranged on the upper left portion of the frame 105 is arranged in the frame 105, and thus the airflow caused by the rotation of the rotating body 113 in the radial direction can be discharged smoothly along the casing 141 out of the frame 105, an inside of the frame 105 can be efficiently kept in a predetermined temperature range under increased heat conditions because of improved function and application of the X-ray CT system and other various working conditions.

Since heat generated by the rotating body 113 can be efficiently exhausted to outside of the rotating body 113 and further outside of the frame 105, the cooling fans (not shown) secured to the parts 107 and the cooling fans 117 secured to the frame 105 can be reduced in number.

In the fifth embodiment, although a location of a suction port 141a is not designated particularly, it is desired that, in order to prevent contrast medium from entering into the frame 105, like the second embodiment, the suction ports 141a may be provided in the upper half (in the range between nine o'clock to three) of the radiographic port 103, otherwise, like the third embodiment, at least part of the radiographic port 103 may be formed as the double wall structure and the suction ports 141a may then be formed in the double wall structure.

What is claimed is:

1. An X-ray CT system comprising:
   a rotating body arranged to be rotated around a subject with said subject as a center, and having a plurality of X-ray tubes arranged around a through hole in which said subject is to be inserted; and
   a frame for housing said rotating body therein, and having a radiographic port which is arranged in compliance with said through hole to pick up images of said subject;
   wherein guide plates are arranged in said frame to guide airflow.

2. An X-ray CT system comprising:
   a rotating body arranged to be rotated around a subject with said subject as a center, and having a plurality of X-ray tubes arranged around a through hole in which said subject is to be inserted;
   a frame for housing said rotating body therein, and having a radiographic port which is arranged in compliance with said through hole to pick up images of said subject; and
   a casing arranged in said frame to cover said rotating body, said casing having suction ports arranged on said radiographic port side to introduce air and delivery ports arranged toward the rotation direction of said rotating body so as to discharge air;
   wherein holes are arranged in said radiographic port to coincide with said suction ports and holes are arranged in said frame to coincide with said delivery ports.

3. An X-ray CT system as claimed in claim 2, wherein said holes arranged in said radiographic port are provided in at least part of an upper half area of said radiographic port.

4. An X-ray CT system as claimed in claim 2, wherein at least a part of said radiographic port is formed as a double wall structure, and said holes for said radiographic port are provided in said double wall structure.

5. An X-ray CT system as claimed in claim 2, wherein at least part of an upper half of said radiographic port is formed as a double wall structure, and said holes for said radiographic port are provided in said double wall structure.

6. An X-ray CT system comprising:
   a rotating body arranged to be rotated around a subject with said subject as a center, and having an X-ray tube arranged around a through hole in which said subject is to be inserted; and
   a frame for housing said rotating body therein, and having a radiographic port which is arranged in compliance with said through hole to pick up an image of said subject;
   wherein suction ports are arranged on an upper side of a central portion in said radiographic port so as to introduce air into said frame.

7. An X-ray CT system comprising:
   a rotating body arranged to be rotated around a subject with said subject as a center, and having an X-ray tube arranged around a through hole in which said subject is to be inserted; and
   a frame for housing said rotating body therein, and having a radiographic port which is arranged in compliance with said through hole to pick up an image of said subject;
   wherein suction ports are arranged in a neighborhood of a central portion in said radiographic port so as to introduce air into said frame, and a part of the central portion of said radiographic port is formed as a double wall structure to form said suction ports.

8. An X-ray CT system comprising:
   a rotating body arranged to be rotated around a subject with said subject as a center, and having an X-ray tube arranged around a through hole in which said subject is to be inserted; and
   a frame for housing said rotating body therein, and having a radiographic port which is arranged in compliance with said through hole to pick up an image of said subject;
   wherein at least part of said radiographic port is formed as a double wall structure in which suction ports for said radiographic port are provided at a neighborhood of a central portion of said frame to introduce air into the central portion of said frame.

* * * * *